United States Patent [19]

Croll

[11] Patent Number: 4,655,712
[45] Date of Patent: Apr. 7, 1987

[54] DENTAL TRAY LIGHT SHIELD

[76] Inventor: Theodore P. Croll, 685 South Chubb Dr., Doylestown, Pa. 18901

[21] Appl. No.: 761,491

[22] Filed: Aug. 1, 1985

[51] Int. Cl.⁴ ............................................. A61C 19/02
[52] U.S. Cl. .................................... 433/229; 350/1.1; 350/311; 350/318
[58] Field of Search ................. 433/229, 141; 350/1.1, 350/311, 318, 639, 143, 372, 528, 571, 576, 587, 638

[56] References Cited

U.S. PATENT DOCUMENTS 1,584,105  5/1926  Lenz ..................................... 350/639
2,816,047  12/1957 Mahler ................................. 350/311

Primary Examiner—Gene Mancene
Assistant Examiner—Adriene J. Lepiane
Attorney, Agent, or Firm—Gregory J. Gore

[57] ABSTRACT

A light shield for protecting dental bonding materials comprises a light filtering coverplate, a stand, and an electronic timer. This device is to be used in a dental operatory to prevent premature curing of the restorative materials after mixing as they await handling and use.

4 Claims, 2 Drawing Figures

DENTAL TRAY LIGHT SHIELD

FIELD OF INVENTION

This invention relates to operatory equipment used in dental medicine. More specifically, this invention relates to a light shield to be used with composite resin bonding material.

BACKGROUND OF INVENTION

The latest developments in modern dentistry have brought about the extensive use of dentin and enamel bonding as a method of restoring human teeth with natural appearing restorative material. Dentin and enamel bonding requires the use of visible light polymerized composite resins which contain a photosensitive initiator for curing. The bonding agents and bulk resin are supplied in a liquid and putty-like consistency respectively. Once applied to a prepared tooth, a light wand or gun focuses a concentrated beam of visible light to harden the entire resin mass by a photopolymerization process. Because of the sensitive chemistry involved in the resin-curing process, these materials require very careful handling. There is a problem, for instance, with the materials prematurely curing because of exposure to general lighting in the dental operatory. This premature curing usually takes place on the dental treatment tray as the materials await handling and use.

SUMMARY OF INVENTION

It is the principle object of the present invention to provide a device which will prevent the problem of premature resin curing as described above. It is an object of the present invention that this device be transparent so that the physician has, at all times, a visual access to the resin materials. It is further object of the instant invention that the device filter out wavelengths of light which accelerate the resin-curing process. It is a further object of the instant invention that the device be self-supporting and convenient to use. It is a further object of the invention that the instant device incorporate for convenience a timer so that the physician can gauge the timing of the various steps required in the resin-bonding technique and it is a final object of the instant invention that the device may be cold sterilized without damage. The foregoing and other objects and advantages are accomplished according to the details in construction of the instant invention as described further herein.

This tray shield device incorporates principally three (3) separate elements. A coverplate, a removable stand and a detachable electronic timer mechanism. This construction is extremely simple and details of its construction can be readily seen from the figures of drawing included in this application.

The coverplate is constructed of orange plastic. This plastic has been shown to filter out the wavelengths of light which most effect the resin-curing process yet, at the same time, permit the transmission of visible light so that all the materials that may be beneath this coverplate for protection can be readily seen. The shape of the coverplate is basically rectangular with rounded corners. However, this shape is not critical to the invention. A stand is provided by a detachable clip at one end of the coverplate. This stand allows the coverplate to be raised above the working surface on an angle so that materials may easily be accommodated beneath. The fact that the coverplate is angled allows materials of different heights to be accommodated yet be positioned close to the coverplate for maximum protection against reflected light. The stand is readily detachable so that the coverplate can be cold sterilized and also so that the unit may be inexpensively manufactured and shipped without damage. The tray shield also includes a convenient electronic timer at one corner of the shield so that the dental practitioner may keep an accurate timing of the various steps required in the resin-cured bonding process.

DESCRIPTION OF THE PREFERRED EMBODIMENT

Figure 1:
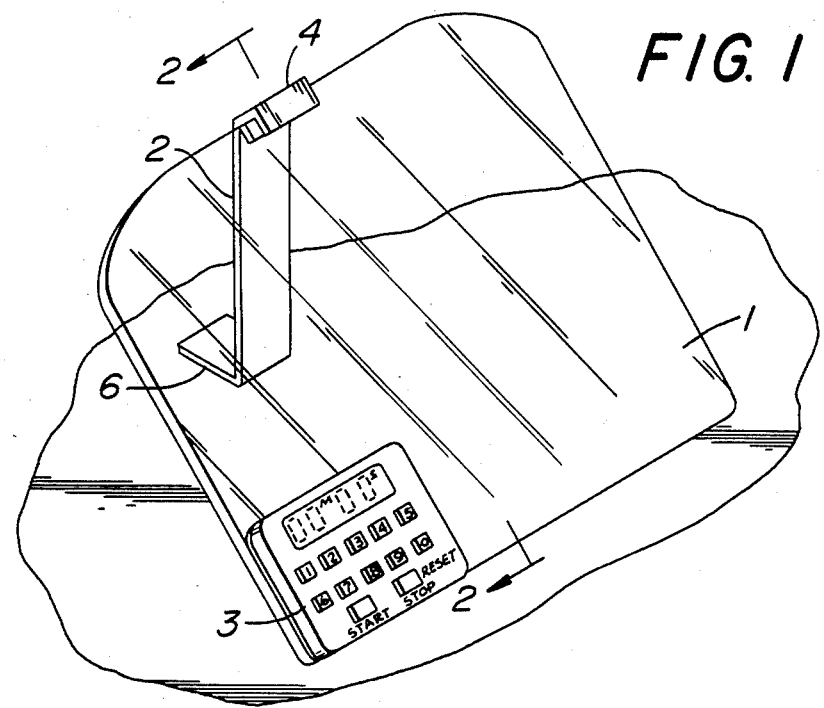
FIG. 1 is an isometric view of the instant invention.
Figure 2:
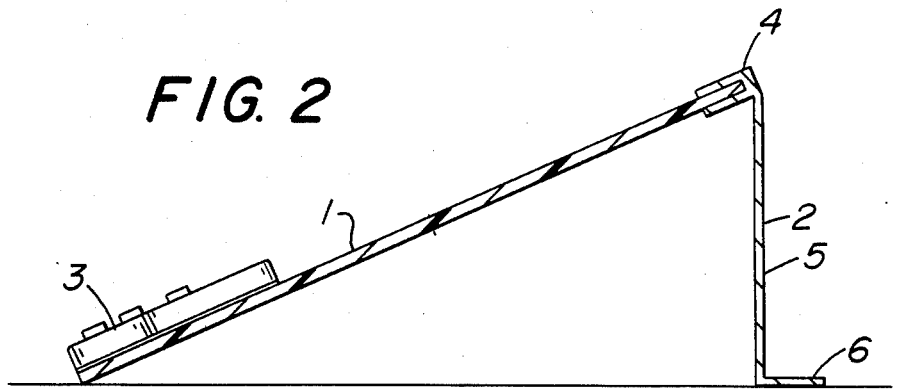
FIG. 2 is a cross-section taken from FIG. 1.

Coverplate 1 is approximately ¼-inch thick and is of a plastic material of the type sold by Rohm & Haas Corporation under the designation orange Plexiglas G (R). Stand element 2 has a simple "Z" configuration with clip means 4 at the top of the stand for detachable connection to the coverplate. The stand has a vertical support portion 5 and a foot 6. The height of the stand may vary but should be greater than the maximum height required for materials to be placed underneath the coverplate. At the end, opposite where the stand is attached, the straight portion of the coverplate rests upon the working surface area. This provides a generally wedge-shaped volume underneath the coverplate, which is protected from the general operatory light which may pre-cure the resin-bonding materials. The coverplate plastic has been shown to filter out UVA light rays in the 400-530 nanometer range, which is frequency of light which cures the resin materials. Other light frequencies are readily transmitted and, therefore, all materials protected underneath the coverplate can be readily seen.

A timer mechanism 3 is located at the lower left-hand corner of the coverplate. This mechanism is a simple electronic stopwatch-type and is also detachably affixed to coverplate 1. The timer shown is of the type manufactured by the Radio Shack (R), Division of the Tandy Corporation (R), but any substitute timer will suffice, so long as the time in seconds is adequately displayed and there are start and stop inputs on the timing mechanism.

It should be understood that there may be many modifications and adaptations of the specific embodiment of the present invention as described herein and still fall within the scope and sphere of the invention. It is therefore intended that the scope of the invention be determined by the appended claims and their legal equivalents.

What is claimed is:

1. A protective cover for use in the preparation of resin-bonding dental materials, comprising;
   (a) coverplate constructed of a transparent material which filters out frequencies of light in the 400-530 nanometer range,
   (b) a stand detachably affixed to said coverplate, said stand having a foot, a vertical support portion and a clamp portion, and
   (c) a timing device affixed to said coverplate.

2. The protective cover of claim 1 wherein the coverplate is made of plastic.

3. The protective cover of claim 2 wherein said stand supports the coverplate at an angle so that a wedge shaped space is created beneath the coverplate to receive materials to be protected.

4. The protective cover of claim 3 wherein said timing device is an electronic timer with a visual display and start and stop controls.

* * * * *